United States Patent [19]

Plöger

[11] 4,117,090
[45] Sep. 26, 1978

[54] PROCESS OF STABILIZATION OF DIBASIC CALCIUM PHOSPHATE DIHYDRATE AGAINST HYDROLYSIS WITH AZACYCLOALKANE-2,2-DIPHOSPHONIC ACIDS

[75] Inventor: Walter Plöger, Hilden, Germany

[73] Assignee: Henkel Kommanditgesellschaft auf Aktien, Düsseldorf-Holthausen, Germany

[21] Appl. No.: 636,732

[22] Filed: Dec. 1, 1975

[30] Foreign Application Priority Data

Nov. 30, 1974 [DE] Fed. Rep. of Germany ....... 2456666

[51] Int. Cl.$^2$ ...................... C01B 15/16; C01B 25/26
[52] U.S. Cl. ..................................... 423/268; 423/308; 423/311; 424/57; 423/265
[58] Field of Search ................. 423/299–323, 423/308–311, 265, 268; 424/49, 52, 57, 128

[56] References Cited

U.S. PATENT DOCUMENTS 3,941,772  3/1976  Ploger et al. ...................... 424/54 X Primary Examiner—O. R. Vertiz
Assistant Examiner—Gregory A. Heller
Attorney, Agent, or Firm—Hammond & Littell

[57] ABSTRACT

A process for stabilizing dibasic calcium phosphate dihydrate against hydrolysis comprising treating an aqueous suspension of dibasic calcium phosphate dihydrate at a pH of from 5 to 10 with an azacycloalkane-2,2-diphosphonic acid of the formula

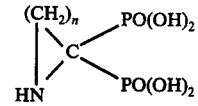

wherein $n$ is an integer from 3 to 5, or a water-soluble salt thereof, in an amount of from 0.01% to 5% by weight with reference to the dibasic calcium phosphate dihydrate; as well as tooth cleaning preparations containing the stabilized dibasic calcium phosphate dihydrate.

5 Claims, No Drawings

PROCESS OF STABILIZATION OF DIBASIC CALCIUM PHOSPHATE DIHYDRATE AGAINST HYDROLYSIS WITH AZACYCLOALKANE-2,2-DIPHOSPHONIC ACIDS

RELATED ART

Dibasic calcium phosphate dihydrate having the formula $CaHPO_4 \cdot 2H_2O$ is a polishing substance frequently utilized in tooth cleaning preparations as, for example, toothpastes and powders. For this purpose it may be used alone or in admixture with other polishing substances as, for example, silica gel or plastics cleaning substances. Besides having some properties advantageous for this purpose, however, the calcium-hydrogenphosphate-dihydrate has the disadvantage that it is not stable to aqueous hydrolysis. This lack of stability to hydrolysis has a particularly aggravating effect in preparations containing water as, for example, toothpastes. However, also in products such as tooth powders it may lead to undesired results. In the presence of moisture, dibasic calcium phosphate dihydrate hydrolyzes easily with liberation of acid, in which case basic phosphates are formed, which mostly have an apatite structure. The processes which thereby take place may be theoretically represented by the following empirical reaction:

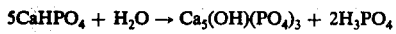

$$5CaHPO_4 + H_2O \rightarrow Ca_5(OH)(PO_4)_3 + 2H_3PO_4$$

In this reaction the dihydrate water of crystallization has been disregarded. The speed as well as the end point of this reaction is influenced by several circumstances such as temperature, pH of the mixture and its composition. The temperature has a particularly great influence, since the dibasic calcium phosphate dihydrate decomposes at temperatures as low as from 36° C. with formation of anhydrous dibasic calcium phosphate, hydroxy-apatite, phosphonic acid and water, or respectively, some calcium phosphate solution. Consequently, the possibility results that even toothcleaning preparations produced without addition of water can hydrolyze. Temperatures of 36° C. and over, moreover, may easily occur in the making of the preparations containing dibasic calcium phosphate dihydrate or, for example, in the storage of finished products, especially in tropical zones.

The acid liberated in the hydrolysis not only, in some cases, alters the pH value of the mixture, but it may change the whole structure of the product; for example, it may cause a paste to solidify; powders may stick together or agglomerate, and tablets may disintegrate. If, in addition to the dibasic calcium phosphate dihydrate, carbonates are present in the mixture, as may be the case with tooth cleaning preparations, during the hydrolysis evolution of carbon dioxide occurs as a very unpleasant side phenomenon, which in some cases may lead to bursting of the container, as for example, tubes, or at least to an expansion or bulge.

For the use of a polishing agent as cleaning material in toothcleaning preparations, its abrasive behavior is of decisive importance, since products to be used for this purpose must only have an abrasive power which does not cause damage to the teeth. Owing to its favorable abrasive behavior, dibasic calcium phosphate dihydrate already enjoys great popularity as a cleaning material in tooth cleaning preparations. If, however, a conversion into the substantially harder apatite is caused by the hydrolysis, in some circumstances abrasive agents or agents with uncontrolled abrasive power may be formed.

Therefore, earlier attempts have already been made to stabilize dibasic calcium phosphate dihydrate against hydrolysis, in order to make possible its use in tooth cleaning agents without any problems. For this purpose various compounds such as pyrophosphoric acid, sodium calcium pyrophosphate or sodium pyrophosphate have been added to a suspension of dibasic calcium phosphate dihydrate in water, the suspension was then filtered and the product obtained was incorporated in the tooth cleaning preparations. All these stabilizing compounds were not satisfactory, howver, since in some cases complicated further treatments of the products were necessary in order to obtain a sufficient stability, and in other cases the process itself caused considerable technical difficulties.

It has further been proposed to use specific phosphonic acids, such as 1-hydroxyethane-1,1-diphosphonic acid or amino-tris-(methylenephosphonic acid) as stabilizers against hydrolysis of dibasic calcium phosphate dihydrate. These phosphonic acids as well as other phosphoinc acids mentioned in this connection, however, have two essential disadvantages in respect to the stabilization of dibasic calcium phosphate dihydrate. Their stabilizing action still leaves much to be desired and the stabilization raises technical problems. Only products with the greatest possible long lasting inhibiting action are suitable for the use as stabilizer of dibasic calcium phosphate dihydrate for tooth cleaning preparations, since the inhibiting action of the phosphonic acids only lasts a certain time, and then usually stops suddenly. In the case of the already proposed phosphonic acids the inhibiting action is not particularly great and does not last sufficiently long. Further, there is the disadvantage that the inhibiting action of the said phosphonic acids does not increase in every case with the increase of the amount added, but on the contrary falls off again, owing to which the desired dosing is technically difficult to carry out.

OBJECTS OF THE INVENTION

An object of the present invention is the development of a process for stabilizing dibasic calcium phosphate dihydrate against hydrolysis consisting essentially of suspending dibasic calcium phosphate dihydrate in an aqueous medium at a pH of from 5 to 10, containing from 0.01% to 5% by weight based on the content of said dibasic calcium phosphate dihydrate of an azacycloalkane-2,2-diphosphonic compound selected from the group consisting of (A) compounds of the formula

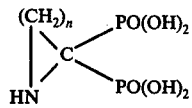

wherein n is an integer from 3 to 5, and (B) water-soluble salts thereof, and separating said stabilized dibasic calcium phosphate dihydrate.

Another object of the present invention is the obtaining of a stabilized dibasic calcium phosphate dihydrate.

A further object of the present invention is the obtaining of tooth cleaning preparations containing a stabilized dibasic calcium phosphate dihydrate.

These and other objects of the present invention will become more apparent as the description thereof proceeds.

DESCRIPTION OF THE INVENTION

It has now been found that a satisfactory and easily effect stabilization of dibasic calcium phosphate dihydrate against hydrolysis is possible by treating the dibasic calcium phosphate dihydrate in aqueous medium at a pH of from 5 to 10, preferably from 6 to 8, with an azacycloalkane-2,2-diphosphonic acid of the general formula

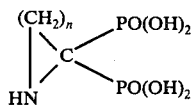

in which $n$ is an integer of from 3 to 5, or a water-soluble salt thereof, in an amount of from 0.01% to 5% by weight, preferably from 0.03% to 2% by weight, referred to the amount of dibasic calcium phosphate dihydrate employed.

More particularly, the invention relates to a process for stabilizing dibasic calcium phosphate dihydrate against hydrolysis consisting essentially of suspending dibasic calcium phosphate dihydrate in an aqueous medium at a pH of from 5 to 10, containing from 0.01% to 5% by weight based on the content of said dibasic calcium phosphate dihydrate of an azacycloalkane-2,2-diphosphonic compound selected from the group consisting of (A) compounds of the formula

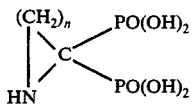

wherein $n$ is an integer from 3 to 5, and (B) water-soluble salts thereof, and separating said stabilized dibasic calcium phosphate dihydrate; as well as the stabilized dibasic calcium phosphate dihydrate so produced and tooth cleaning preparations containing the same.

In carrying out the process of the invention the azacycloalkane-2,2-diphosphonic acid or its water-soluble salt, the dibasic calcium phosphate dihydrate and water may be admixed in any manner. For example, the azacycloalkane-2,2-diphosphonic acid or its water-soluble salt may be used in the mixture either as an aqueous solution or in solid form and the dibasic calcium phosphate dihydrate may be used in the mixture either as an aqueous suspension or in solid form.

The preparation of the azacycloalkane-2,2-diphosphonic acids to be used according to the present invention, or their water-soluble salts may be carried out in a simple way by reacting a lactam of the formula

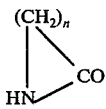

in which $n$ represents an integer of from 3 to 5, with phosphorus trihalides or mixtures of phosphorus trihalides and phosphorous acid, hydrolyzing the reaction product and if desired converting into the salts, as are described in copending commonly assigned U.S. patent application Ser. No. 499,000, filed Aug. 20, 1974, now Pat. No. 3,941,772.

The reaction is generally effected at temperatures from 40° to 150° C. Suitable starting substances are, for example, pyrrolidone ($n=3$), piperidone ($n=4$) and caprolactam ($n=5$), which are readily available as commercial products.

The reaction may be carried out, for example, by first melting the lactam with phosphorous acid and slowly adding $PCl_3$ with stirring. The mostly viscous reaction product formed is then hydrolyzed by addition of water. However, the molten lactam can also be reacted directly with phosphorus trihalides and hydrolyzed in stages. Suitable phosphorus trihalides are especially phosphorus trichloride and phosphorus tribromide. The latter has been found particularly suitable when lactams are used without addition of phosphorous acid. The molar ratio of lactam: phosphorus compound in the reactions described ranges from 1:2 to 1:6, preferably 1:4.

The hydrolysis is suitably effected by addition of water to the reaction mixture. If desired, however, it may also be carried out in the presence of alkali, such as especially caustic soda or caustic potash.

Advantageously the cyclic aminophosphonic acids may also be employed in the form of their water-soluble salts such as their alkali metal salts, especially lithium, sodium and potassium salts, and their ammonium salts. The conversion into the salts may easily be carried out by partial or complete neutralization with the corresponding bases.

The stabilization according to the present invention may either be carried out before isolation of the dibasic calcium phosphate dihydrate from the reaction medium in which it is prepared or in a later separate treatment process. The preparation of the dibasic calcium phosphate dihydrate may be effected according to processes known from the literature, for example, from calcium hydroxide and phosphoric acid.

If the stabilization is to be carried out on previously isolated dibasic calcium phosphate dihydrate which is the preferred method of production, this previously isolated dibasic calcium phosphate dihydrate is treated with an aqueous solution of the stabilizer, the pH of the solution being adjusted to from 5 to 10, preferably from 6 to 8. However, even if the stabilization is effected before isolation of the dibasic calcium phosphate dihydrate from the reaction medium, the aqueous suspension is set at a pH of 5 to 10, preferably 6 to 8, with the addition of the stabilizer. The amount of stabilizer required can easily be found by testing. It has been found that in general 0.01% to 5% by weight, preferably 0.03% to 2% by weight, based on the amount of dibasic calcium phosphate dihydrate to be stabilized is sufficient in the event no other stabilizers are present. The amount, within the indicated limits, is dependent on (a) the extent of the desired stabilization, (b) the particle size, surface and surface structure of the dibasic calcium phosphate dihydrate prepared, and (c) the time of contact between the stabilizer and the product to be stabilized. It has further been found suitable to use the water-soluble salts of the azacycloalkane-2,2-diphosphonic acids, for example, alkali metal salts, especially sodium salts. If the free acids are to be used, it may be necessary to correct for pH deviations, for example, by addition of calcium hydroxide or calcium oxide. Owing to the small amounts of the added azacycloalkane-2,2- diphosphonic acid, however, this is often unnecessary. The stabilizers to be used according to the present invention may also be used in combination with other substances, such as other stabilizers, aids to precipitation or protective colloids as, for example, with pyrophosphates, tripolyphosphates and other polymeric phosphates, polysilicates, polycarboxylates, lignin derivatives, gums and polysaccharides.

Cyclic aminophosphonic acids of the above-mentioned general formula which are also substituted on the nitrogen atom also show a stabilizing action, but this is substantially less and, therefore, of little technical interest.

The present invention relates primarily to the preparation of a dibasic calcium phosphate dihydrate stabilized against hydrolysis, for use in tooth cleaning preparations. Such stabilized products, however, may also be advantageous in other fields of application. The tooth cleaning preparations to be prepared according to the present invention may contain, in addition to the stabilized dibasic calcium phosphate dihydrate serving as polishing material, the usual constituents such as, for example, thickeners, surface-active compounds or tensides, emulsifiers, bactericides, and flavoring substances. A toothpaste is the preferred form of the tooth cleaning preparations with a content of stabilized dibasic calcium phosphate dihydrate according to the present invention.

Toothpastes are generally pasty preparations based on water, which contain thickeners, wetting and foaming agents, moisture-retention agents, polishing, scouring or cleaning substances, aroma-imparting substances, taste correctors, antiseptic and other substances valuable as mouth cosmetics. The content of polishing substances in the toothpastes, i.e., the content of the dibasic calcium phosphate dihydrate which is to be used according to the present invention and which is stabilized against hydrolysis, will generally vary from 25% to 60% by weight, referred to the total mass of the toothpaste. The wetting and foaming agents employed are especially soap-free anionic surface-active compounds such as fatty alcohol sulfates, for example, sodium lauryl sulfate, mono-glyceride sulfates, sodium lauryl sulfoacetate, sarcosides, taurides and other anionic surface-active compounds which do not affect the taste, in amounts from 0.5% to 5% by weight. For the preparation of the binder for toothpaste, all thickeners usual for this purpose may be used, such as hydroxyethylcellulose, sodium carboxymethylcellulose, tragacanth, carrageen moss, agar-agar and gum arabic, as well as additionally finely divided silicic acids, all in amounts of from 0.1% to 5% by weight of the whole toothpaste. As moisture-retention means, glycerine and sorbitol are of principal importance, in amounts which may be up to one-third or from 5% to 33 1/3% by weight of the whole toothpaste. Water is also present in amounts of from 10% to 50% by weight of the whole toothpaste. With toothpowders, the water, thickeners and moisture-retention means are omitted. The desired aroma and taste requirements can be attained by an addition of essential oils such as peppermint, clove, wintergreen and sassafras oils, as well as by sweetening agents, such as saccharin, dulcin, dextrose or laevulose.

In addition fluorine-containing compounds serving for the control of caries or for caries prophylaxis may be present. These are present in amounts of from 0 to 2% measured as fluorine ions of the whole tooth cleaning preparations. Such fluorine-containing compounds are, for example, sodium fluoride, potassium fluoride, aluminum fluoride, ammonium fluoride, monoethanolamine-hydrofluoride, hexadecylamine-hydrofluoride, oleylamine-hydrofluoride, N,N',N'-tri-(polyoxyethylene)-N-hexadecyl-propylenediamine-dihydrofluoride, bis-(hydroxyethyl)-amino-propyl-N-hydroxyethyl-octadecylamine-dihydrofluoride, magnesium aspartate-hydrofluoride, and tin fluoride. Also fluorine compounds in which the fluorine is present primarily in a preponderantly non-ionic bond, which, however, may split off fluoride, for example, by hydrolysis or other chemical reactions, such as sodium monofluorophosphate, potassium monofluorophosphate, magnesium monofluorophosphate, indium fluorozirconate, zirconium hexafluorogermanate, etc.

Optionally further cleaning and filling substances possibly also used in the tooth cleaning preparations are present, as for example, plastics particles, silica gels or pyrogenic silicic acids.

The preparation of the dibasic calcium phosphate dihydrate against hydrolysis is generally effected by treatment of a previously isolated dibasic calcium phosphate dihydrate with an aqueous solution of the stabilizer. It is, of course, also possible to stabilize a dibasic calcium phosphate dihydrate present in an already finished toothpaste subsequently against the reaction with fluorine ions by an addition thereto of salts of azacycloalkane-2,2-diphosphonic acids. Such measures may be employed in special circumstances, but should remain confined to exceptions, since the results of such a difficultly controllable treatment in a heterogeneous system like a toothpaste is not always fully guaranteed.

The following Examples further illustrate the present invention, without however being restricted thereto.

EXAMPLES

Firstly the preparation of some azacycloalkane-2,2-diphosphonic acids to be used as stabilizers according to the present invention is described.

Stabilizer A: Preparation of azacyclopentane-2,2-diphosphonic acid ($n=3$)

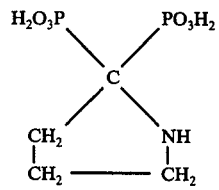

85.0 gm (1.0 mol) of 2-pyrrolidone and 164 gm (2.0 mol) of $H_3PO_3$ were melted at 80° C. 176 ml (2.0 mol) of $PCl_3$ were dropped in with stirring. The mixture was stirred for a further 3 hours and left overnight at 70° C. Then it was hydrolyzed with 3 liters of $H_2O$. The solution was boiled with activated charcoal and after filtration, the reaction product was precipitated with acetone. The white substance was dissolved in water and passed through a cation exchanger. Thereafter the solution was concentrated and the substance isolated by addition of ethanol. The yield of crystalline azacyclopentane-2,2-diphosphonic acid was 95 gm Δ 41% of theory.

The molecular weight of the compound was determined titrimetrically as 230 (calculated 231.09).

In the infra-red spectrum the compound showed a $\delta_{NH}$ band at 1615 cm$^{-1}$ and had a melting point of 277° C.

Stabilizer B: Preparation of
azacyclohexane-2,2-diphosphonic acid ($n=4$)

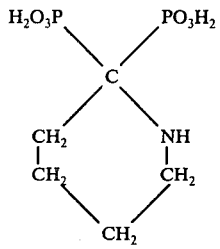

49.5 gm (0.5 mol) of 2-piperidone and 82 gm (1.0 mol) of H$_3$PO$_3$ were melted at 70° C. and, as described in the case of Stabilizer A, reacted with 88 ml of PCl$_3$. The reaction mixture was similarly worked up. The yield of crystalline azacyclohexane-2,2-diphosphonic acid was 28 gm, 21% of theory.

After drying at 60° C. in a drying oven, the compound was isolated as the monohydrate. The titrimetrically determined molecular weight is 261 (calculated 263.1).

The anhydrous compound was obtained after drying at 80° C. over P$_2$O$_5$. The infra-red spectrum showed the $\delta_{NH}$ band at 1585 cm$^{-1}$, m.p. 249° C.

Stabilizer C: Preparation of
azacycloheptane-2,2-diphosphonic acid ($n=5$)

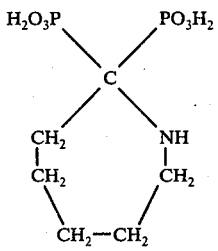

113 gm (1.0 mol) of caprolactam and 164 gm (2.0 mol) of H$_3$PO$_3$ were heated at 100° C. to give a clear melt. After cooling to 70° C., the mixture was further reacted with 176 ml (2.0 mol) of PCl$_3$, as described for Stabilizer A. The reaction mixture was similarly worked up. The yield of crystalline azacycloheptane-2,2-diphosphonic acid, sparingly soluble in water, was 84 gm Δ 32% of theory.

After drying at 80° C. in a vacuum drying oven the aazcycloheptane-2,2-diphosphonic acid had a molecular weight of 260, obtained titrimetrically (calculated 259.1).

In the infra-red spectrum the compound showed the $\delta_{NH}$ band at 1610 cm$^{-1}$, m.p. 257° C.

The following Examples serve to demonstrate the superior activity of the azacycloalkane-2,2-diphosphonic acids to be used as stabilizers according to the present invention. In these the products stabilized according to the present invention were not only compared with untreated dibasic calcium phosphate dihydrate, but also compared with products which were obtained by treatments with other structurally different phosphonic acids.

As a measure of the stabilizing action the hydrolysis of the dibasic calcium phosphate dihydrate in an aqueous suspension was followed at 60° C. The acid formed during the hydrolysis was continuously back-titrated with alkali, owing to which a constant pH value of the hydrolysis solution was ensured during the whole hydrolysis. The consumption of alkali was continuously followed over the entire period and consequently gave at each point of time a measure for the progress of the hydrolysis. The consumption of alkali may also be given in percentages of the final consumption, which then corresponds to the percentage rate of phosphate which is hydrolyzed at the respective point of time. The titration over the given time can advantageously be carried out by means of a recording auto-titrator, which is arranged for pH-stat measurements.

In order to be able to compare truly the individual experiments, it is not only necessary during the measurements to keep constant, for example, the parameters of temperature, pH, amount of dibasic calcium phosphate dihydrate and amount of solution, but also the same dibasic calcium phosphate dihydrate must always be used.

This requirement was fulfilled in the present case in that, according to the directions of Johnson and Rathlev (in Bailor, "Inorganic Syntheses", Vol. 4, New York-Toronto-London 1953, pages 1/218, 20) a large quantity of well crystallized dibasic calcium phosphate dihydrate was prepared and the fraction of particle size between 0.5 and 1 mm was sieved out and employed in the following.

EXAMPLE 1

3.7 mg of azacycloheptane-2,2-diphosphonic acid (0.037%, based on the CaHPO$_4$.2H$_2$O employed) were dissolved in 10 ml of water. The solution was adjusted with NaOH to pH 7.5 and made up to 25 ml with water. 15 ml of barbital buffer of pH 7.6 were added thereto. Then 10 gm of dibasic calcium phosphate dihydrate were suspended in this solution, left for 24 hours in the solution, then filtered off by suction, washed with a little water and alcohol and dried.

In the same way dibasic calcium phospate dihydrate was prepared which had been treated respectively with 12 mg (0.12% based on the CaHPO$_4$.2H$_2$O) of the following phosphonic acids:
1-Hydroxyethane-1,1-diphosphonic acid
N-Methylaminomethanediphosphonic acid
2-Phosphonopropane-1,2-dicarboxylic acid
Dimethylaminomethanediphosphonic acid.

A similar sample was also made without addition of phosphonic acid.

2.58 gm of each of these treated dibasic calcium phosphate dihydrates were mixed in a temperature controlled vessel with 3 ml of a barbital buffer solution of pH 7.6 and 7 ml of water. To this was added a mixture heated to about 80° C. of 7 ml of barbital buffer pH 8 and 33 ml of water. A CaHPO$_4$.2H$_2$O suspension at 60° C. and a pH of 7.5 was thereby obtained. The pH of the suspension was kept constant by means of an automatic titrator by addition of NaOH and the consumption of alkaline liquor caused by the hydrolysis was recorded over the entire hydrolysis period. The following times of hydrolysis resulted for the individual products, which are shown in the following Table 1.

TABLE 1

| Inhibitor | | Time for x % hydrolysis (minutes) | | | | | |
|---|---|---|---|---|---|---|---|
| | | 10% | 20% | 40% | 60% | 80% | 100% |
| Without addition | | 7.5 | 7.8 | 8.0 | 8.2 | 8.3 | 9.4 |
| 0.037 % | Azacycloheptane-2,2-diphosphonic acid | 62 | 64 | 67 | 69 | 72 | 90 |
| 0.12 % | 1-Hydroxyethane-1,1-diphosphonic acid | 54 | 56 | 57 | 60 | 65 | 86 |
| 0.12 % | N-Methylaminomethane-1,1-diphosphonic acid | 32 | 34 | 36 | 38 | 39 | 46 |
| 0.12 % | 2-Phosphonopropane-1,2-dicarboxylic acid | 9 | 10 | 12 | 16 | 23 | 35 |
| 0.12 % | Dimethylaminomethane-diphosphonic acid | 11 | 12 | 14 | 18 | 24 | 35 |

The measured results show clearly that only 1-hydroxyethane-1,1-diphosphonic acid (HEDP) attains a good inhibiting effect comparable with the compound according to the present invention, but here only with use of more than three times the quantity of HEDP as the azacycloheptane-2,2-diphosphonic acid.

EXAMPLE 2

As in Example 1, dibasic calcium phosphate dihydrates were prepared which were treated with the following amounts of inhibitors:

0.037% Azacyclopheptane-2,2-diphosphonic acid
0.24% 1-Hydroxyethane-1,1-diphosphonic acid
0.24% 2-Phosphonopropane-1,2-dicarboxylic acid
0.24% Dimethylaminomethanediphosphonic acid The measurements of the times of hydrolysis corresponding to Example 1 produced the results given in Table 2.

TABLE 2

| Inhibitor | | Time for x% hydrolysis (minutes) | | | | | |
|---|---|---|---|---|---|---|---|
| | | 10% | 20% | 40% | 60% | 80% | 100% |
| 0.037 % | Azacycloheptane-2,2-diphosphonic acid | 62 | 64 | 67 | 69 | 72 | 90 |
| 0.24 % | 1-Hydroxyethane-1,1-diphosphonic acid | 28 | 31 | 34 | 37 | 39 | 43 |
| 0.24 % | 2-Phosphonopropane-1,1-dicarboxylic acid | 10 | 13 | 15 | 19 | 26 | 40 |
| 0.24 % | Dimethylaminomethane-diphosphonic acid | 14 | 15 | 17 | 22 | 28 | 40 |

In comparison with Example 1 this series of measurements shows that in spite of further considerable increase of the concentration used of the phosphonic acids taken for comparison these did not show any substantially stronger action, but on the contrary, in the case of the 1-hydroxyethane-1,1-diphosphonic acid a decline is noted.

EXAMPLE 3

Dibasic calcium phosphate dihydrates were prepared as in Example 1, which were treated with the following amounts of inhibitor:

0.037% Azacycloheptane-2,2-diphosphonic acid
0.6% 1-Hydroxyethane-1,1-diphosphonic acid
0.6% N-Methylaminomethanediphosphonic acid
0.6% 2-Phosphonopropane-1,2-dicarboxylic acid
0.6% Dimethylaminomethanediphosphonic acid The measurement of the times of hydrolysis corresponding to Example 1 gave the values shown in the following Table.

TABLE 3

| Inhibitor | | Time for x% hydrolysis (minutes) | | | | | |
|---|---|---|---|---|---|---|---|
| | | 10% | 20% | 40% | 60% | 80% | 100% |
| 0.037 % | Azacycloheptane-2,2-diphosphonic acid | 62 | 64 | 67 | 69 | 72 | 90 |
| 0.6 % | 1-hydroxyethane-1,1-diphosphonic acid | 27 | 28 | 31 | 34 | 38 | 56 |
| 0.6 % | N-Methylaminomethane-diphosphonic acid | 38 | 40 | 42 | 44 | 46 | 53 |
| 0.6 % | 2-Phosphonopropane-1,2-dicarboxylic acid | 9 | 11 | 13 | 18 | 24 | 35 |
| 0.6 % | Dimethylaminomethane-diphosphonic acid | 9 | 10 | 13 | 18 | 24 | 30 |

Even with considerably over 10 times the amount of the other substances the inhibiting action of the phosphonic acid according to the present invention is not reached.

EXAMPLE 4

Samples of dibasic calcium phosphate dihydrate according to Example 1 were prepared, which were treated with the percentage amounts of different phosphonic acids indicated in Table 4. They were examined as described in Example 1. The results of the measurements are given in the following Table 4.

TABLE 4

| Inhibitor | | Time for x% hydrolysis (minutes) | | | | | |
|---|---|---|---|---|---|---|---|
| | | 10% | 20% | 40% | 60% | 80% | 100% |
| 0.3 % | Azacycloheptane-2,2-diphosphonic acid | 105 | 435 | 750 | 755 | 765 | 775 |
| 0.3 % | N-Methylpyrrolidone-5,5-diphosphonic acid | 16 | 17 | 20 | 24 | 30 | 45 |
| 0.3 % | 1-Methyl-2-hydroxy-2-oxo-3-methylamino-3-phosphono-6-oxo-1,2-azaphosphacyclohexane | 10 | 11 | 14 | 18 | 22 | 32 |
| 0.3 % | 2-Phosphonobutane-1,2,4-tricarboxylic acid | 14 | 15 | 18 | 23 | 31 | 40 |
| 0.3 % | Pyrrolidone-5,5-diphosphonic acid | 11 | 12 | 14 | 18 | 23 | 33 |

In this experiment the distinct superiority is shown of the azacycloheptane-2,2-diphosphonic acid with respect to the inhibiting action on use of the same percentage amounts in comparison with other phosphonic acids.

EXAMPLE 5

Dibasic calcium phosphate dihydrate samples were prepared according to Example 1, which were treated with the percentages of inhibitor indicated in Table 5. They were examined as described in Example 1. The results of the measurements are given in the following Table 5.

TABLE 5

| Inhibitor | | Time for x% hydrolysis (minutes) | | | | | |
|---|---|---|---|---|---|---|---|
| | | 10% | 20% | 40% | 60% | 80% | 100% |
| 0.75 % | Azacycloheptane-2,2-diphosphonic acid | 100 | 315 | 1040 | 1110 | 1115 | 1130 |
| 0.75 % | 1-Hydroxyethane-1,1-diphosphonic acid | 26 | 28 | 30 | 34 | 38 | 56 |
| 0.75 % | N-Methylpyrrolidone-5,5-diphosphonic acid | 11 | 12 | 14 | 18 | 24 | 40 |
| 0.75 % | Amino-tri-(methylene-phosphonic acid) | 15 | 17 | 20 | 24 | 28 | 35 |
| 0.75 % | Ethylenediamino-tetra-(methylenephosphonic acid) | 56 | 60 | 65 | 68 | 72 | 80 |
| 0.75 % | N-Methylaminoethane-diphosphonic acid | 36 | 38 | 41 | 43 | 46 | 50 |
| 0.75 % | Pyrrolidone-5,5-diphosphonic acid | 10 | 11 | 13 | 17 | 22 | 30 |

In this series of experiments the extraordinary superiority of the substance according to the present invention is shown still more clearly than in Example 4.

EXAMPLE 6

A $CaHPO_4.2H_2O$ cleaning material already stabilized by known means and commercially obtainable was treated according to the process described in Example 1 additionally with 0.75% of the phosphonic acids according to the present invention and the hydrolysis was measured. The additional stabilization against hydrolysis given therefrom was compared with a sample not additionally treated and with a sample which was treated with a phosphonic acid already known for this purpose. It was shown that the compounds according to the present invention undergo a distinct additional inhibition, which is far superior to that of already known compounds. The values obtained in the measurements are given in the following Table 6.

TABLE 6

| Additional inhibitor | | Time for 100% hydrolysis (minutes) |
|---|---|---|
| | without | 140 |
| 0.75 % | Amino-tris-(methylene-phosphonic acid) | 185 |
| 0.75 % | Azacycloheptane-2,2-diphosphonic acid | 635 |
| 0.75 % | Azacyclopentane-2,2-diphosphonic acid | 1095 |

In the following examples formulations for tooth cleaning preparations are given which contain dibasic calcium phosphate dihydrate stabilized according to the present invention as a polishing material.

EXAMPLE 7

Composition of a toothpaste according to the present invention.

| | Parts by Weight |
|---|---|
| Glycerine | 30.0 |
| Water | 18.0 |
| Sodium carboxymethylcellulose | 1.0 |
| Dibasic calcium phosphate dihydrate stabilized with 1% of azacycloheptane-2,2-diphosphonic acid | 36.0 |
| Insoluble sodium metaphosphate | 10.0 |
| Sodium lauryl sulfate | 1.0 |
| Pyrogenic silicic acid | 1.5 |
| Sodium monofluorophosphate | 0.5 |
| Essential oils | 1.5 |
| Saccharin sweetener | 0.5 |

Instead of Stabilizer C used in the above formulation for stabilizing the dibasic calcium phosphate dihydrate Stabilizers A and B can be used in the same amounts with the same good results

EXAMPLE 8

Composition of a tooth powder according to the present invention.

| | Parts by Weight |
|---|---|
| Dibasic calcium phosphate dihydrate stabilized with 1% of azacycloheptane-2,2-diphosphonic acid | 50.0 |
| Precipitated chalk | 30.0 |
| Finely divided silicic acid | 10.0 |
| Milk sugar | 4.0 |
| Precipitated magnesium carbonate | 4.0 |
| Titanium dioxide | 1.0 |
| Tannin | 1.0 |

Instead of the Stabilizer C used in the above formulation for the stabilization of the dibasic calcium phosphate dihydrate, Stabilizers A and B may be used in the same amount with the same good results.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for stabilizing dibasic calcium phosphate dihydrate against hydrolysis consisting essentially of suspending dibasic calcium phosphate dihydrate in an aqueous medium at a pH of from 5 to 10, containing from 0.01% to 5% by weight based on the content of said dibasic calcium phosphate dihydrate of an azacycloalkane-2,2-diphosphonic compound selected from the group consisting of (A) compounds of the formula

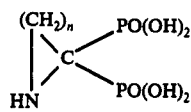

wherein $n$ is an integer from 3 to 5, and (B) water-soluble salts thereof, and separating said stabilized dibasic calcium phosphate dihydrate.

2. The process of claim 1 wherein said pH is between 6 and 8.

3. The process of claim 1 wherein the amount of said azacycloalkane-2,2-diphosphonic compound is from 0.03% to 2% by weight based on the content of said dibasic calcium phosphate dihydrate.

4. The process of claim 1 wherein said water-soluble salts are selected from the group consisting of the alkali metal salts and ammonium salts.

5. A dibasic calcium phosphate dihydrate stabilized against hydrolysis by an azacycloalkane-2,2-diphosphonic compound produced by the process of suspending dibasic calcium phosphate dihydrate in an aqueous medium at a pH of from 5 to 10, containing from 0.01% to 5% by weight based on the content of said dibasic calcium phosphate dihydrate of an azacycloalkane-2,2-diphosphonic compound selected from the group consisting of (A) compounds of the formula

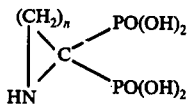

wherein $n$ is an integer from 3 to 5, and (B) water-soluble salts thereof, and separating said stabilized dibasic calcium phosphate dihydrate.

* * * * *

UNITED STATES PATENT AND TRADEMARK OFFICE
CERTIFICATE OF CORRECTION

PATENT NO. : 4,117,090
DATED : September 26, 1978
INVENTOR(S) : Walter Ploger

It is certified that error appears in the above-identified patent and that said Letters Patent are hereby corrected as shown below:

Item [56]   References Cited

After "3,941,772   3/1976   Ploger et al   424/54 X" the following patents cited in Paper No. 2 should be inserted:

| | | | |
|---|---|---|---|
| 3,792,152 | 2/1974  | Kim            | 423/311 |
| 3,442,604 | 5/1969  | Smith et al    | 23/108  |
| 3,169,096 | 2/1965  | Schlaeger et al| 424/57  |
| 3,066,056 | 11/1962 | Schlaeger et al| 23/108  |
| 3,012,852 | 12/1961 | Nelson         | 23/109  |
| 2,018,410 | 10/1935 | McDonald et al | 424/57  |
| 3,678,154 | 7/1972  | Widder et al   | 424/52  |
| 3,488,419 | 1/1970  | McCune et al   | 424/49  |
| 3,308,029 | 3/1967  | Saunders et al | 424/52  |
| 2,876,166 | 3/1959  | Nebergall      | 424/52  |
| 3,244,478 | 4/1966  | Stahlheber     | 423/311 |

UNITED STATES PATENT AND TRADEMARK OFFICE
CERTIFICATE OF CORRECTION

PATENT NO. : 4,117,090

DATED : September 26, 1978

INVENTOR(S) : Walter Ploger

It is certified that error appears in the above-identified patent and that said Letters Patent are hereby corrected as shown below:

Column 6, line 65, "$\Delta$" should read --$\underline{\Delta}$--.

Column 7, line 53, "$\Delta$" should read --$\underline{\Delta}$--.

Signed and Sealed this

Seventh Day of August 1979

[SEAL]

Attest:

LUTRELLE F. PARKER

*Attesting Officer*   *Acting Commissioner of Patents and Trademarks*